(12) United States Patent
Fudulova et al.

(10) Patent No.: US 12,078,703 B2
(45) Date of Patent: Sep. 3, 2024

(54) AUTOMATED FIELD OF VIEW ALIGNMENT FOR MAGNETIC RESONANCE IMAGING

(71) Applicant: KONINKLIJKE PHILIPS N.V., Eindhoven (NL)

(72) Inventors: Irina Fudulova, Moscow (RU); Fedor Mushenok, Moscow (RU)

(73) Assignee: Koninklijke Philips N.V., Eindhoven (NL)

(*) Notice: Subject to any disclaimer, the term of this patent is extended or adjusted under 35 U.S.C. 154(b) by 372 days.

(21) Appl. No.: 17/610,455

(22) PCT Filed: May 16, 2020

(86) PCT No.: PCT/EP2020/063744
§ 371 (c)(1),
(2) Date: Nov. 11, 2021

(87) PCT Pub. No.: WO2020/234204
PCT Pub. Date: Nov. 26, 2020

(65) Prior Publication Data
US 2022/0225888 A1 Jul. 21, 2022

(30) Foreign Application Priority Data

May 17, 2019 (EP) .................................... 19175092
Jul. 2, 2019 (RU) ............................... 2019120557

(51) Int. Cl.
*G06V 10/25* (2022.01)
*A61B 5/00* (2006.01)
(Continued)

(52) U.S. Cl.
CPC .......... *G01R 33/543* (2013.01); *A61B 5/0037* (2013.01); *A61B 5/055* (2013.01);
(Continued)

(58) Field of Classification Search
CPC .... G06V 10/25; G06V 10/82; G06V 2201/03; G06V 2201/10; A61B 5/7264
See application file for complete search history.

(56) References Cited

U.S. PATENT DOCUMENTS 11,191,281 B1 * 12/2021 Foreman .................. B26D 7/08
11,868,672 B1 * 1/2024 Dehkordi .............. G06F 3/1446
(Continued)

FOREIGN PATENT DOCUMENTS

WO 2014136017 A1 9/2014

OTHER PUBLICATIONS

Yokosawa et al "Automated Scan Plane Planning for Brain MRI Using 2D Scout Images" Proc. Intl. Soc. Mag. Reson. Med 18 p. 3136 (2010).
(Continued)

*Primary Examiner* — Ming Y Hon

(57) ABSTRACT

Disclosed herein is a medical system (100, 300, 500) comprising a memory (110) storing machine executable instructions (120) and a predictor algorithm (122) configured for outputting predicted field of view alignment data (128) for a magnetic resonance imaging system (502) in response to inputting one or more localizer magnetic resonance images (124) and subject metadata (126). The predictor algorithm comprises a trainable machine learning algorithm. The medical system further comprises a processor (104) configured for controlling the medical system. Execution of the machine executable instructions causes the processor to: receive (200) the one or more localizer magnetic resonance images and the subject metadata; and receive (202) the predicted field of view alignment data from the predictor algorithm in response to inputting the one or more localizer magnetic resonance images into the predictor algorithm and in response to inputting the subject metadata.

12 Claims, 7 Drawing Sheets

(51) Int. Cl.
 *A61B 5/055* (2006.01)
 *G01R 33/54* (2006.01)
 *G01R 33/56* (2006.01)
 *G06F 18/214* (2023.01)
 *G06V 10/82* (2022.01)

(52) U.S. Cl.
 CPC .......... *A61B 5/7235* (2013.01); *A61B 5/7425* (2013.01); *G01R 33/5608* (2013.01); *G06F 18/214* (2023.01); *G06V 10/25* (2022.01); *G06V 10/82* (2022.01); *G06V 2201/03* (2022.01); *G06V 2201/10* (2022.01)

(56) References Cited

U.S. PATENT DOCUMENTS

| | | | | |
|---|---|---|---|---|
| 11,868,852 | B1* | 1/2024 | Watson | H04L 63/10 |
| 2015/0043774 | A1* | 2/2015 | Harder | G06V 10/141 |
| | | | | 382/128 |
| 2018/0035892 | A1 | 2/2018 | Lu et al. | |
| 2019/0302205 | A1* | 10/2019 | Stainsby | G01R 33/3875 |
| 2019/0347790 | A1* | 11/2019 | Lee | A61B 5/0075 |
| 2019/0377047 | A1* | 12/2019 | Chen | G01R 33/5608 |
| 2020/0294287 | A1* | 9/2020 | Schlemper | G06T 11/006 |
| 2021/0137384 | A1* | 5/2021 | Robinson | A61B 6/032 |
| 2021/0156940 | A1* | 5/2021 | Sommer | G01R 33/543 |
| 2021/0201077 | A1* | 7/2021 | Lwowski | G06V 10/774 |
| 2022/0087533 | A1* | 3/2022 | El-Sallam | G06N 20/00 |
| 2022/0392111 | A1* | 12/2022 | Sztuk | G06F 3/012 |

OTHER PUBLICATIONS

S. Young "Automated Planning of MRI Neuro Scans" Proceedings of SPIE Mar. 2006.

Polzin et al "Intelligent Scanning Using Deep Learning for MRI-Tensor Flow-Medium" Mar. 7, 2019 p. 1-8.

Wang et al "TIENET: Text Image Embeding Network for Common Thorax Disease Classification and Reporting in Chest X-Rays" 2018 IEEE/CVF Conf. on Computer Vision and Pattern Recognition Jun. 18, 2018 p. 9049-9058.

Zhang et al "Deep Cross Modal Projection Learning for Image-Text Matching" Perfasive: International Conf. on Pervasive Computing Oct. 6, 2018 p. 707-723.

Wang "Learning Two-Branch Neural Networks for Image-Text Matching Tasks" Computer Science 2017.

International Search Report and Written Opinion From PCT/EP2020/063744 Mailed Nov. 26, 2020.

* cited by examiner

AUTOMATED FIELD OF VIEW ALIGNMENT FOR MAGNETIC RESONANCE IMAGING

CROSS REFERENCE TO RELATED APPLICATIONS

This application is a U.S. national phase application of International Application No. PCT/EP2020/063744 filed on May 16, 2020, which claims the benefit of EP Application Serial No. 19175092.6 filed May 17, 2019 and RU Application Serial No. 2019120557 filed July 2, 2019 and is incorporated herein by reference.

FIELD OF THE INVENTION

The invention relates to Magnetic Resonance Imaging, in particular to planning for magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI. For example, various anatomical or physiological properties of a subject can be investigated using MRI. To image the proper location within a subject preliminary magnetic resonance images which are typically called localizers or scout images are acquired first. The localizers are then used by an operator to properly position a field of view (region of interest) for subsequent scans.

The conference publication et al., (2010). "Automated Scan Plane Planning for Brain MRI using 2D Scout Images," In Proceedings of ISMRM, 2010, p. 3136 discloses the use of an automated algorithm for scan plane planning.

SUMMARY OF THE INVENTION

The invention provides for a medical system, a computer program product, and a method in the independent claims. Embodiments are given in the dependent claims.

A difficulty with automating the positioning of a field of view after a localizer magnetic resonance image is that the initial position of a subject and the subject's anatomy can vary greatly. Trained operators may also have difficulty in placing a field of view consistently to obtain acceptable results in subsequent scans. Embodiments of the invention may solve this problem by using a predictor algorithm that has a trainable machine learning component to position the field of view. The predictor algorithm uses one or more localizer magnetic resonance images and subject metadata as input to generate predicted field of view alignment data. This may have several advantages. Firstly, a medical imaging database containing historical localizer magnetic resonance images, subject data, and the location field of views may be mined for training data.

In one aspect the invention provides for a medical system that comprises a memory storing machine-executable instructions configured for controlling the medical system. The memory further stores a predictor algorithm configured for outputting predicted field of view alignment data in response to inputting one or more localizer magnetic resonance images and subject metadata. The predicted field of view alignment data as used herein encompasses data which may be used for specifying the position of a field of view for a subsequent magnetic resonance imaging scan.

A localizer magnetic resonance image as used herein encompasses a magnetic resonance image which may be used for planning a subsequent magnetic resonance imaging scan. These are typically low-resolution, very wide field of view magnetic resonance images; however, this does not need to be the case as most magnetic resonance images may be used for planning further magnetic resonance imaging scans. The subject metadata as used herein encompasses data which is descriptive of the subject and relevant to the proper execution of the magnetic resonance imaging protocol. For example, the subject metadata may list descriptors of the subject such as the subject's height, weight, gender, suspected medical condition and other parameters. These subject metadata may affect the prediction of the field-of-view alignment data. For example children have different non-mature brain anatomical structures as compared to that of adults. Further, obese patients need larger fields-of-view to visualise abdominal regions in their entirety as compared to a slim patient to be examined.

The predictor algorithm comprises a trainable machine learning algorithm. The medical system further comprises a processor configured for controlling the medical system. Execution of the machine-executable instructions causes the processor to receive the one or more localizer magnetic resonance images and the subject metadata. Both the one or more localizer magnetic resonance images and subject metadata may be received in different ways in different examples. Suitable machine learnable algorithms may be based on deep-learning models which use both images and text (so called text-image embeddings) for training and inference. Practical examples are e.g.: https://zpascal.net/cvpr2018/Wang_TieNet_Text-Image_Embedding_CVPR_2018_paper.pdf, https://arvix.org/pdf/1704.03470.pdf, https://arxiv.org/pdf/1711.05535.pdf, http://openaccess.thecvf.com/content_ECCV_2018/papers/Ying_Zhang_Deep_Cross-Modal_Projection_ECCV_2018_paper.pdf.

Notably, neural networks taking such complex various inputs (images, text, categorical variables) are able to predict the field-of-view settings from input localiser images and patient metadata.

In some cases, receiving may encompass retrieving them from a memory or storage device. In other examples they may be received via a network. In other examples the processor may control such things as a magnetic resonance imaging system to acquire the one or more localizer magnetic resonance images and may for example receive the subject metadata from a storage device for planning a magnetic resonance imaging scan or receive it via a terminal or other user interface.

Execution of the machine-executable instructions further causes the processor to receive the predicted field of view alignment data from the predictor algorithm in response to inputting the one or more localizer magnetic resonance images into the predictor algorithm and in response to inputting the subject metadata. The one or more localizer magnetic resonance images and the subject metadata are input into the predictor algorithm and in response the predictor algorithm provides the predicted field of view alignment data. This may be beneficial because the predicted field of view alignment data may be used for configuring a subsequent magnetic resonance imaging scan. This may for example enable automatic magnetic resonance imaging. It may also be an assistance or a quality control tool that is used when an operator is operating a magnetic resonance imaging system manually.

A medical system as used herein may encompass different types of systems in different examples. In one example the medical system may be a magnetic resonance imaging system and the described embodiments may be integrated into the components of the magnetic resonance imaging system. In another example the medical system may be a workstation which is used for planning and/or analyzing magnetic resonance imaging data and images. In another example the medical system may be a service that is provided through a cloud or cloud computing system via a network or other data exchange interface.

In another embodiment the memory further stores a training data. The training data contains training entries. Each of the training entries comprises one or more training magnetic resonance images, training subject metadata, and training field of view alignment data. The one or more training magnetic resonance images and training subject metadata represent the type of data that would be input into the predictor algorithm. The training field of view alignment data represents the type of data that is output by the predictor algorithm.

The memory further comprises a training algorithm configured for training the predictor algorithm using a comparison between the predicted field of view alignment data and the training field of view alignment data. This comparison may for example be performed in different ways. In some examples the comparison could be made by a trained neural network. In other examples the geometric location of the predicted field of view alignment data and the training field of view alignment data may be compared and quantitized.

Execution of the machine-executable instructions further causes the processor to receive the predicted field of view alignment data from the predictor algorithm in response to inputting the one or more training magnetic resonance images into the predictor algorithm and in response to inputting the training subject metadata. Execution of the machine-executable instructions further cause the processor to train the predictor algorithm using the comparison between the predicted field of view alignment data and the training field of view alignment data. This may be beneficial because it provides a means for improving the accuracy of the predicted field of view alignment data that is output by the predictor algorithm.

In some cases, the determination of the comparison between the predicted field of view alignment data and the training field of view alignment data is performed by the predictor algorithm itself For example, these two pieces of data may be input into the predictor algorithm and the training proceeds automatically. In other cases, execution of the machine-executable instructions may further cause the processor to determine the comparison between the predicted field of view alignment data and the training field of view alignment data using a further algorithm or mathematical comparison. For example, the coordinates and the positioning of the two fields of view may be numerically compared.

In another embodiment execution of the machine-executable instructions further causes the processor to generate the training data by extracting the one more training magnetic resonance image, the training subject metadata, and the training field of view alignment data from a medical image database. Typically, when magnetic resonance imaging protocols are performed, the data from an examination may be stored in a database. For example, the data may be stored from a particular examination in a so-called DICOM file. The data in one example may be extracted from DICOM files. This and the related embodiments may be beneficial because it provides a means of using actual examination data and alignments of field of view to produce or improve the predictor algorithm.

In another embodiment the predictor algorithm is a convolutional neural network. For example, the convolutional neural network may be trained using deep learning. The predicted field of view alignment data may be compared to the training field of view alignment data numerically.

In another embodiment the predictor algorithm comprises a feature extractor configured for providing a feature vector using the subject metadata and the one or more localizer magnetic resonance images. This feature extractor may take different forms in different examples. For example, an algorithm which looks for anatomical landmarks may comprise a feature vector which identifies the location of these anatomical landmarks. Likewise, a deformable shape model or even an anatomical atlas may also be used in such a way. In other examples a neural network may be used to provide a feature vector which may be subsequently used by the trainable machine learning algorithm to output the predicted field of view alignment data.

The trainable machine learning algorithm is configured for outputting the predicted field of view alignment data in response to inputting the feature vector. The use of a feature vector in this manner may be beneficial because it is very transparent and may be readily understood by a doctor or other professional using the medical system. This may reduce how brittle the response of the predictor algorithm is. This may also enable the use of a trainable machine learning algorithm which is more readily understood by a human.

In another embodiment the trainable machine learning algorithm is a decision tree algorithm.

In another embodiment the trainable machine learning algorithm is a k-nearest neighbor algorithm.

The use of the decision tree or the k-nearest neighbor algorithm is beneficial in that a human is able to review the model manually and see if it is safe and/or does not contain data which is misleading or which may cause the predictor algorithm to malfunction or provide false data.

In another embodiment the feature extractor is a trained neural network configured for providing the feature vector. This embodiment may be beneficial because the trained neural network is only used to provide the feature vector and essentially classify the image and locate various landmarks which are then used by the predictor algorithm. This for example may make the operation of the predictor algorithm more transparent and understandable to a human.

In another embodiment the feature extractor is configured for providing the feature vector by fitting a deformable shape model.

In another embodiment the feature extractor is configured for providing the feature vector using an anatomical atlas.

In another embodiment the medical system is a medical imaging workstation.

In another embodiment the medical system is a cloud-based magnetic resonance imaging planning system. For example, a magnetic resonance imaging system or other medical imaging workstation could contact the medical system via the internet or other network connection and send it the subject metadata and the one or more localizer magnetic resonance images and in return receive the predicted field of view alignment data.

In another embodiment the medical system further comprises a magnetic resonance imaging system.

In another embodiment the memory further comprises localizer pulse sequence commands configured for controlling the magnetic resonance imaging system to acquire localizer magnetic resonance imaging data. Execution of the machine-executable instructions further causes the processor to acquire the localizer magnetic resonance imaging data by controlling the magnetic resonance imaging system with the localizer pulse sequence commands. Execution of the machine-executable instructions further causes the processor to reconstruct the one or more localizer magnetic resonance images from the localizer magnetic resonance imaging data. This embodiment may be beneficial because the automated determination of the field of view is incorporated directly into a magnetic resonance imaging system.

In another embodiment the memory further comprises clinical pulse sequence commands configured for controlling the magnetic resonance imaging system to acquire clinical magnetic resonance imaging data. Execution of the machine-executable instructions further cause the processor to generate modified pulse sequence commands by modifying the clinical pulse sequence commands with the predicted field of view alignment data. For example, the field of view in the modified pulse sequence commands could be modified or changed using the predicted field of view alignment data. Execution of the machine-executable instructions further cause the processor to acquire the clinical magnetic resonance imaging data by controlling the magnetic resonance imaging system with the modified pulse sequence commands.

In some examples, execution of the machine-executable instructions may also cause the processor to reconstruct one or more clinical magnetic resonance images from the clinical magnetic resonance imaging data.

In another aspect the invention provides for a computer program product comprising machine-executable instructions for execution by a processor controlling the medical system. The computer program product further comprises an implementation of a predictor algorithm configured for outputting predicted field of view alignment data in response to inputting one or more localizer magnetic resonance images and subject metadata. The predictor algorithm comprises a trainable learning algorithm. Execution of the machine-executable instructions causes the processor to receive the one or more localizer magnetic resonance images and the subject metadata. Execution of the machine-executable instructions causes the processor to receive the predicted field of view alignment data from the predictor algorithm in response to inputting the one or more localizer magnetic resonance images into the predictor algorithm and in response to inputting the subject metadata. The advantages of this embodiment have been previously discussed.

In another aspect the invention provides for a method of operating a medical system. The medical system comprises a memory storing a predictor algorithm. The predictor algorithm is configured for outputting predicted field of view alignment data in response to inputting one or more localizer magnetic resonance images and subject metadata. The predictor algorithm comprises a trainable machine learning algorithm. The memory further stores training data. The training data contains training entries. Each of the training entries comprises one or more training magnetic resonance images, training subject metadata, and training field of view alignment data. The memory further comprises a training algorithm configured for training the particular algorithm using a comparison between the predicted field of view alignment data and the training field of view alignment data.

The method comprises receiving the predicted field of view alignment data from the predictor algorithm in response to inputting the one or more training magnetic resonance images into the predictor algorithm and in response to inputting the training subject metadata. The method further comprises determining the comparison between the predicted field of view alignment data and the training field of view alignment data. The method further comprises training the predictor algorithm with the training algorithm by inputting the comparison between the predicted field of view alignment data and the training field of view alignment data.

In another embodiment the method further comprises generating the training data by extracting the one or more training magnetic resonance images, the training subject metadata, and the training field of view alignment data from a medical image database.

In another embodiment the method further comprises receiving one or more localizer magnetic resonance images and subject metadata. The method further comprises receiving the predicted field of view alignment data from the predictor algorithm in response to inputting the one or more localizer magnetic resonance images into the predictor algorithm and in response to inputting the subject metadata.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
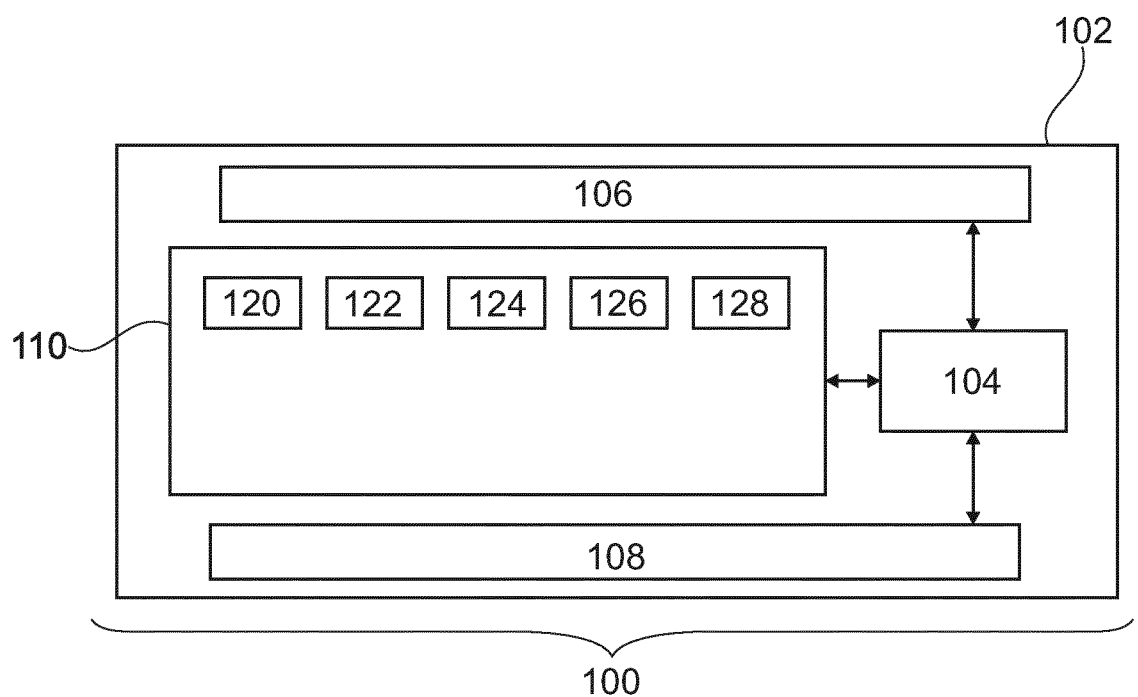
FIG. 1 illustrates an example of a medical system.

FIG. 1 illustrates an example of a medical system 100. The medical system 100 is shown as comprising a computer 102 with a processor 104. The processor 104 is intended to represent one or more processing cores and may be distributed in different computers or computing systems. The processor 104 is connected to a hardware interface 106. The hardware interface 106 may for example be used to enable the processor 104 to connect with and/or control other components of the medical system 100. The hardware interface 106 may also contain elements which enable it to communicate with other computer systems or data systems via a network. The processor 104 is further being shown as connected to an optional user interface 108. The processor 104 is also shown as being connected to a memory 110 here.

The memory 110 may for example represent different types of memory which a processor 104 may have access to. The memory 110 may be any combination of memory which is accessible to the processor 104. This may include such things as main memory, cached memory, and also non-volatile memory such as flash RAM, hard drives, or other storage devices. In some examples the memory 110 may be considered to be a non-transitory computer-readable medium.

The memory 110 is shown as containing machine-executable instructions 120. The machine-executable instructions 120 enable the processor 104 to control the medical system 100. The machine-executable instructions 120 may also enable the processor 104 to perform various data analysis and image processing tasks.

The memory 110 is further shown as containing an implementation of a predictor algorithm 122. The memory is further shown as containing one or more localizer magnetic resonance images 124. The term localizer is used as a global label to identify one or a group of particular magnetic resonance images. The memory 110 is further shown as containing subject metadata 126. The subject metadata 126 is metadata which is descriptive of the subject, the magnetic resonance protocol used to acquire or reconstruct the one or more localizer magnetic resonance images 124 or other data. The memory 110 is further shown as containing a predicted field of view alignment data 128. The predicted field of view alignment data 128 was provided by inputting the subject metadata 126 and the one or more localizer magnetic resonance images 124 into the predictor algorithm 122.

Figure 2:
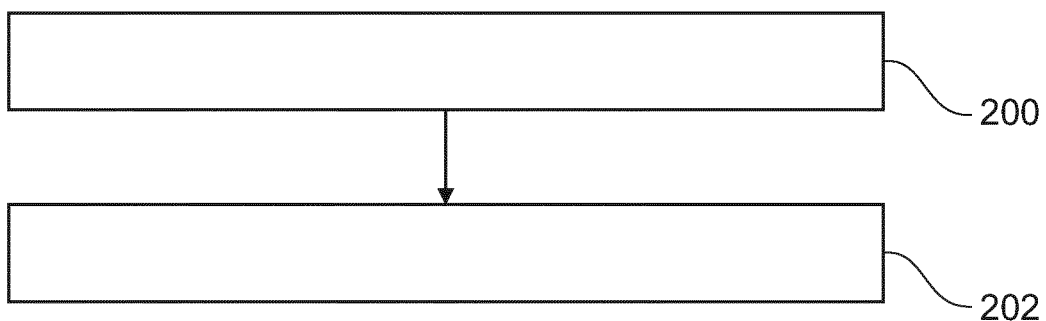
FIG. 2 shows a flow chart which illustrates a method of using the medical system of FIG. 1.

FIG. 2 shows a flowchart which illustrates a method of operating the medical system 100. First in step 200 the one or more localizer magnetic resonance images 124 are received. In step 200 the subject metadata 126 is also received. Next in step 202 the predicted field of view alignment data 128 is provided by inputting the subject metadata 126 and the one or more localizer magnetic resonance images 124 into the predictor algorithm 122.

Figure 3:
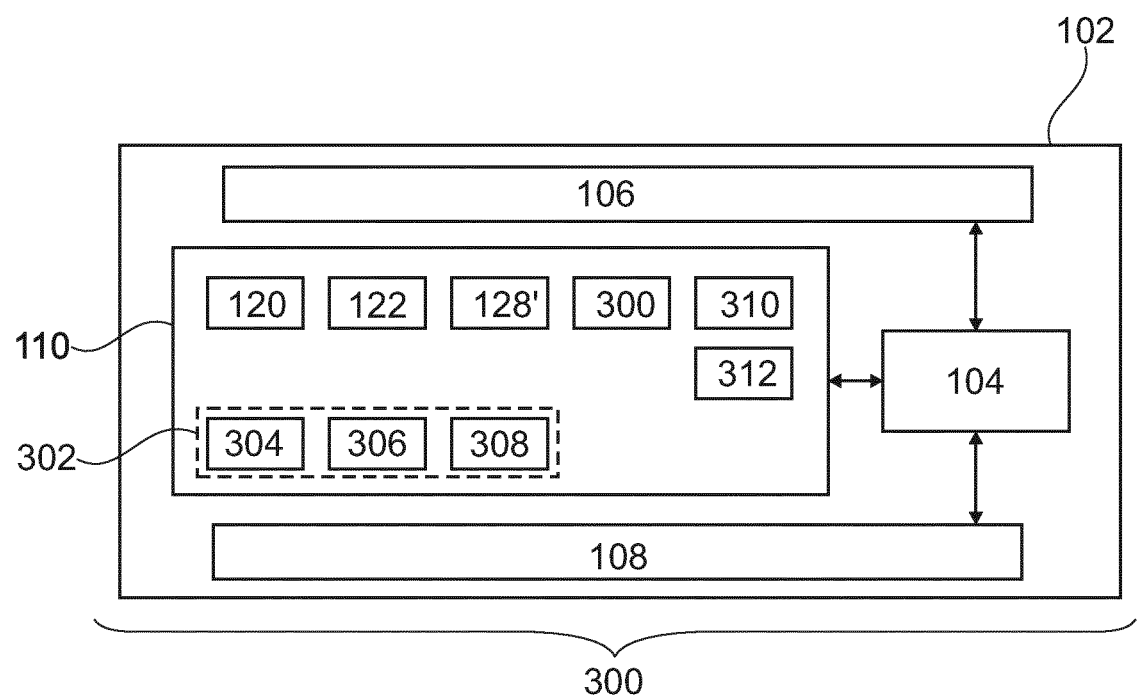
FIG. 3 illustrates a further example of a medical system.

FIG. 3 illustrates a further example of a medical system 300. It should be noted that the features of the medical system 100 in FIG. 1 and the medical system 300 in FIG. 3 may be freely combined. This may be in the form of combining all the elements into a single computer system or the systems 100, 300 illustrated in FIGS. 1 and 3 may be connected via a network connection.

In FIG. 3 the memory 110 is again shown as containing machine-executable instructions 120 and the predictor algorithm 122. The memory 110 is further shown as containing predicted field of view alignment data 128'. The memory 110 is further shown as containing a training algorithm 300 which is configured for modifying or training the predictor algorithm 122. The memory 110 is further shown as containing one or more training entries 302. Each training entry 302 contains one or more training magnetic resonance images 304, training subject metadata 306, and training field of view alignment data 308.

The one or more training magnetic resonance images 304 and the training subject metadata 306 may be input into the predictor algorithm 122 to provide the predicted field of view alignment data 128. The predicted field of view alignment data 128' may then be compared to the training field of view alignment data 308 and a comparison 310 may be made. For example, the field of view alignment data may comprise the coordinates and/or orientation of the field of view. The comparison 310 can be a numerical comparison of these coordinates and orientations. The comparison 310 may then be input into the training algorithm 300 which then uses this to modify the predictor algorithm 122. In some examples the comparison functionality is integrated directly into the training algorithm 300. In this case the system functions by inputting the predicted field of view alignment data 128' and the training field of view alignment data 308 directly into the training algorithm 300 which then goes and modifies the predictor algorithm 122.

The memory 110 is further shown as optionally containing a medical imaging database 312. The medical imaging database 312 may for example provide archive data such as DICOM images and other data and metadata that was acquired during the use of a magnetic resonance imaging system. In some instances, the machine-executable instructions 120 are programmed to mine or extract the training entries 302 from data contained within the medical imaging database 312.

Figure 4:
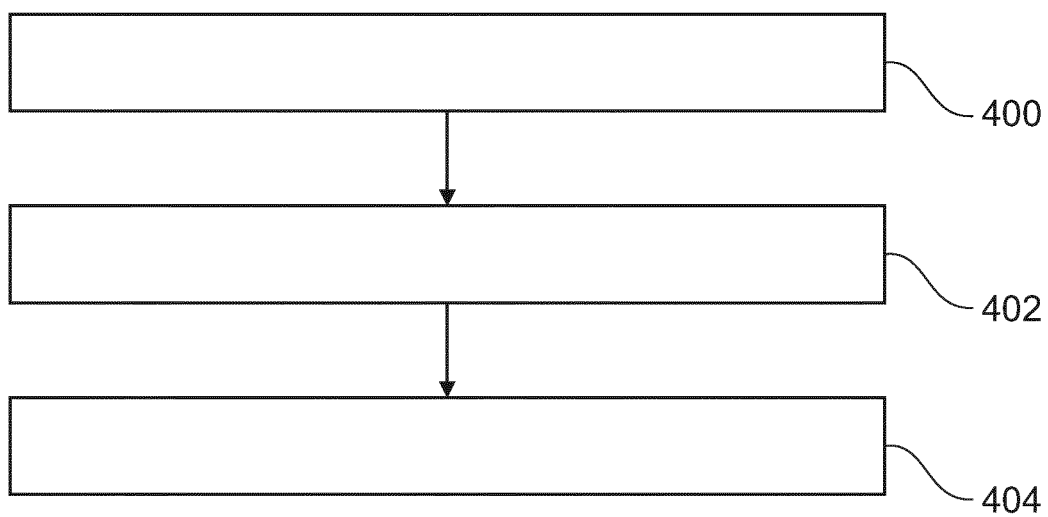
FIG. 4 shows a flow chart which illustrates a method of using the medical system of FIG. 3.

FIG. 4 shows a flowchart which illustrates a method of operating the medical system 300 of FIG. 3. The method of FIG. 4 may be combined with the method of FIG. 3. For example, the steps of FIG. 3 may be performed before or after the steps contained in FIG. 4.

First in step 400 the predicted field of view alignment data 128 is received by inputting the one or more training magnetic resonance images 304 and the training subject metadata 306 into the predictor algorithm 122. Next in step 402 the comparison 310 is calculated by comparing the training field of view alignment data 308 with the predicted field of view alignment data 128'. Finally, in step 404, the predictor algorithm 122 uses the comparison 310 to train or modify the predictor algorithm 122. The exact method of modifying the predictor algorithm 122 depends upon the type of predictor algorithm. If the predictor algorithm comprises a trainable machine learning algorithm then the type of algorithm determines how it is trained.

Figure 5:
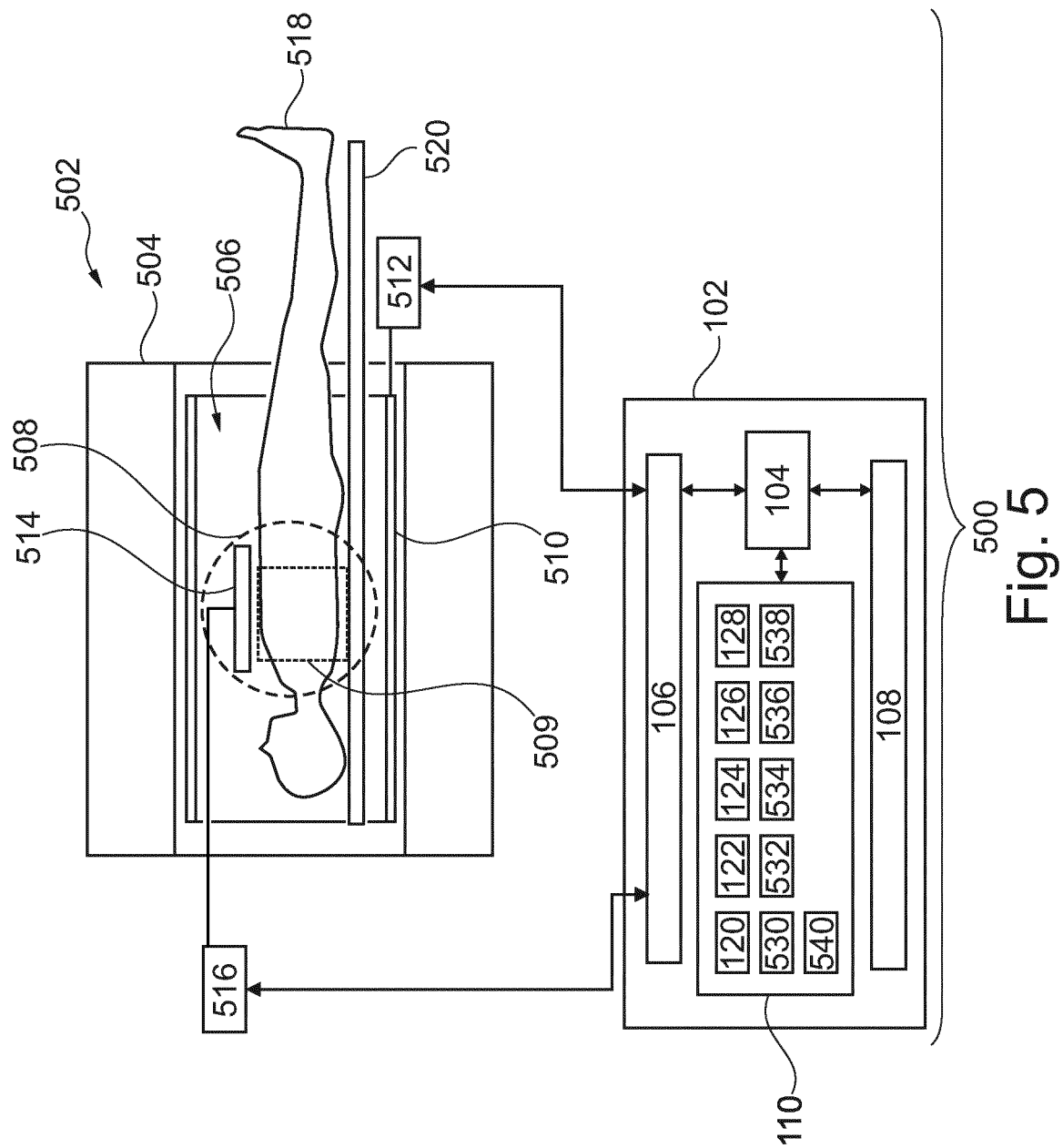
FIG. 5 illustrates a further example of a medical system.

FIG. 5 illustrates a further example of a medical system 500. In this example the medical system 500 further comprises a magnetic resonance imaging system 502. It should be noted that the features of the medical system 300 illustrated in FIG. 3 may also be freely combined with the features illustrated in FIG. 5.

The magnetic resonance imaging system 502 comprises a magnet 504. The magnet 504 is a superconducting cylindrical type magnet with a bore 506 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 506 of the cylindrical magnet 504 there is an imaging zone 508 where the magnetic field is strong and uniform enough to perform magnetic resonance imaging. A region of interest 509 is shown within the imaging zone 508. The magnetic resonance data that is acquired typically acquired for the field of view. A subject 518 is shown as being supported by a subject support 520 such that at least a portion of the subject 518 is within the imaging zone 508 and the region of interest 509.

Within the bore 506 of the magnet there is also a set of magnetic field gradient coils 510 which is used for acquisition of preliminary magnetic resonance data to spatially encode magnetic spins within the imaging zone 508 of the magnet 504. The magnetic field gradient coils 510 connected to a magnetic field gradient coil power supply 512. The magnetic field gradient coils 510 are intended to be representative. Typically magnetic field gradient coils 510 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Adjacent to the imaging zone 508 is a radio-frequency coil 514 for manipulating the orientations of magnetic spins within the imaging zone 508 and for receiving radio transmissions from spins also within the imaging zone 508. The radio frequency antenna may contain multiple coil elements. The radio frequency antenna may also be referred to as a channel or antenna. The radio-frequency coil 514 is connected to a radio frequency transceiver 516. The radio-frequency coil 514 and radio frequency transceiver 516 may be replaced by separate transmit and receive coils and a separate transmitter and receiver. It is understood that the radio-frequency coil 514 and the radio frequency transceiver 516 are representative. The radio-frequency coil 514 is intended to also represent a dedicated transmit antenna and a dedicated receive antenna. Likewise the transceiver 516 may also represent a separate transmitter and receivers. The radio-frequency coil 514 may also have multiple receive/transmit elements and the radio frequency transceiver 516 may have multiple receive/transmit channels. For example if a parallel imaging technique such as SENSE is performed, the radio-frequency could 514 will have multiple coil elements.

The transceiver 516 and the gradient controller 512 are shown as being connected to the hardware interface 106 of a computer system 102.

The memory 110 is further shown as containing localizer pulse sequence commands 530. The memory is further shown as containing localizer magnetic resonance imaging data 532 that was acquired by controlling the magnetic resonance imaging system 502 with the localizer pulse sequence commands 530. The memory 110 is further shown as containing the one or more localizer magnetic resonance images 124. They were reconstructed from the localizer magnetic resonance imaging data 532. The medical system 500 is illustrated as containing all of the features of the medical system 100 of FIG. 1.

The memory 110 is further shown as containing clinical pulse sequence commands 534. The predicted field of view alignment data 128 may be used to modify pulse sequence commands to set or modify the field of view. The memory 110 is further shown as containing modified pulse sequence commands 536 that were made by modifying the clinical pulse sequence commands 534 with the predicted field of view alignment data 128. The memory 110 is further shown as containing clinical magnetic resonance imaging data 538 that was acquired by controlling the magnetic resonance imaging system 502 with the modified pulse sequence commands 536. The memory 110 is further shown as optionally containing clinical magnetic resonance image 540 that was reconstructed from the clinical magnetic resonance imaging data 538.

Figure 6:
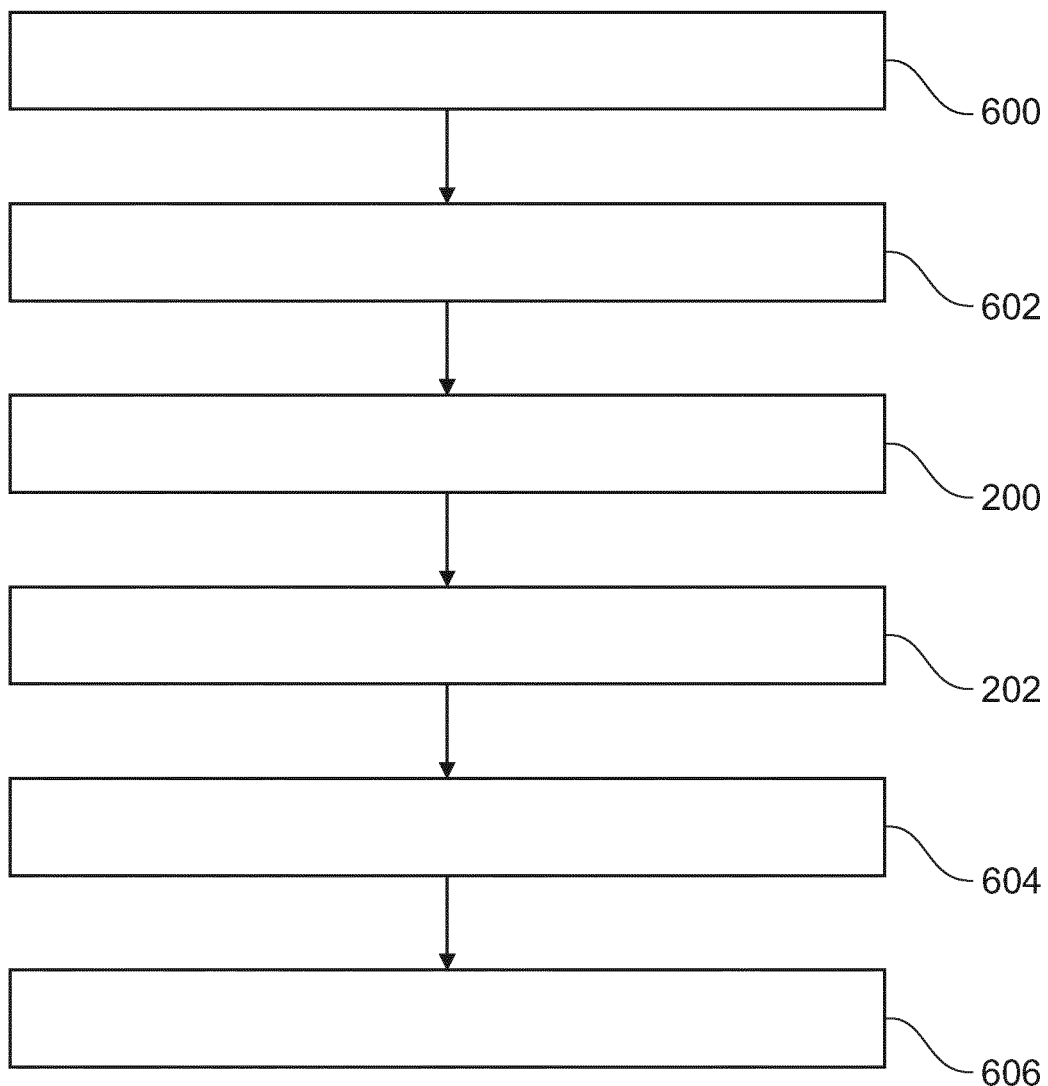
FIG. 6 shows a flow chart which illustrates a method of using the medical system of FIG. 5.

FIG. 6 shows a flowchart which illustrates a method of operating the medical system 500 of FIG. 5. First in step 600, the localizer magnetic resonance imaging data 532 is acquired by controlling the magnetic resonance imaging system 502 with the localizer pulse sequence commands 530. Next in step 602 the one or more localizer magnetic resonance images 124 are reconstructed from the localizer magnetic resonance imaging data 532. Next steps 200 and 202 as illustrated in FIG. 2 are performed. After step 202 the method proceeds to step 604. In step 604 the modified pulse sequence commands 536 are generated or created by modifying the clinical pulse sequence commands 534 with the predicted field of view alignment data 128. Finally, in step 606 the clinical magnetic resonance imaging data 538 is acquired by controlling the magnetic resonance imaging system 502 with the modified pulse sequence commands 536.

Planning is a preliminary step of each MRI study on which the quality of clinical images (clinical magnetic resonance images 540) can depend. Automation of planning may allow one to achieve high repeatability of images' orientation for quantitative comparison of follow-up studies. Examples may provide a new approach for training of automatic sequence planning algorithm that exploits content of radiological datasets. Examples may allow developing and training automatic sequence planning algorithms without pre-built anatomical models and involvement of expert knowledge.

A lot of time and efforts of radiological stuff are spent on planning of MR studies. The purpose of the planning is to center a field of view (FOV) of MR scanner relative to a region of interest (ROI) (509) and to orient scanning planes along the anatomical axes of organs and systems of a subject (518). Planning allows one to maximize information, reduce an impact of the patient's position and individual anatomical peculiarities on clinical images and to show images from convenient point of view. Main steps of sequence planning may include one or more of the following:
1. Obtaining of low-resolution localizer images in three orthogonal planes.
2. Visual recognition and marking of anatomical landmarks.
3. Aligning of the FOV relative to recognized anatomical landmarks. All consequent clinical images are taken in newly aligned field of view.

Examples may provide a new approach for development of automatic sequence planning algorithm.

Manual sequence planning is fast and cost-effective preliminary step of MR study, but it has a few disadvantages. The most important disadvantages of manual planning include:
1) Human-dependent accuracy. Accuracy of sequence planning is an essential requirement for comprehensive and reliable MRI study. However, it strongly depends on qualification of medical stuff and there isn't an easy way to control it.
2) Lack of repeatability. Repeatability of sequence planning is a key requirement for quantitative analysis and comparison of follow-up studies. However, there is a significant inter- and intra-patient variability of FOV orientation and it is almost impossible to make sure that follow-up scans are being manually aligned in the same orientation as a preceding study.

A possible way to overcome these disadvantages is through automatic sequence planning (ASP) algorithms. Purpose of these algorithms is to automatically suggest a uniform and highly repeatable orientation of FOV in spite of peculiarities of patient anatomy and his/her position. So far, a bunch of ASP algorithms have been proposed, developed and implemented in commercial products. All of them are based on pre-built anatomical models of human body and exploits automatic recognition of anatomical landmarks. As a result, existing ASP algorithms require expert medical knowledge and cannot be easily adapted to preferences and practices of a particular medical organization. The proposed examples may allow the development and training of automatic sequence planning algorithms (prediction algorithm 122) possibly without pre-built anatomical models and possibly without involvement of expert knowledge.

A possible element of examples is a new approach for training of automatic sequence planning (ASP) algorithm that exploits content of radiological datasets. Most existing radiological datasets contain localizers (or scout images), patient metadata (age, sex, weight etc.) and clinical images of different modalities. The localizers show region of interest (ROI) in an initial position before FOV alignment and sequence planning. The clinical images show the same ROI after sequence planning and contain information about applied alignment steps (for example, relative shift and tilting of scanning planes). Therefore, a radiological dataset can be considered as a collection of pairs of initial patient position and optimal FOV orientation for the given position. In other word, such collections represent an implicit form of expert knowledge that can be extracted by modern algorithms of machine learning (for instance, k-nearest-neighbors, regression, computer vision, etc.). During training of a machine learning algorithm localizer images and patient metainformation are features; position and orientation of clinical images are target values. Once the algorithm was optimized in this fashion, it is applied to new localizer images and produces position of origin and orientation of FOV for subsequent radiological studies.

Examples may comprise of a predictor (predictor algorithm 122) and optionally teacher (training algorithm 300) (see FIG. 7 below). The predictor comprises a machine learning algorithm (trainable machine learning algorithm) that receives localizer images as an input and returns optimal position and orientation of FOV for subsequence clinical images. Many modern machine learning algorithms (k-nearest-neighbors, decision trees, convolution networks, etc.) can be used as a predictor. The teacher is an algorithm that compares actual and predicted values of FOV position and orientation, estimate degree of discrepancy between real and predicted values and modifies the predictor thus to decrease the discrepancy. The goal of predictor's modification may possibly be to achieve highest accuracy and precision of target values. The specific implementation of the teacher depends on the selected predictor.

Embodiments may be applicable for planning of radiological studies of any part of a subject. To build the invention one or more of the following steps may be performed:
1. Collect and prepare suitable train radiological dataset. Localizer images and patient metainformation act as features, spatial FOV orientation of consequent clinical images acts as target ground-true value.
2. Select a predictor architecture that allows prediction of spatial orientation of FOV using selected features.
3. Optimize parameters of the predictor to minimize discrepancy of predicted and real orientations of FOV.
4. Store the ASP algorithm and its optimized parameters on a writable medium such as a computer hard drive.

To use examples one or more of the following steps may be performed:
1. Collect available patient metainformation and obtain localizer images with suitable radiological equipment.
2. Load the stored ASP algorithm and its optimized parameters.
3. Send patient metainformation and localizer images to the predictor.
4. Get predicted optimal FOV orientation.
5. Align FOV using proposed optimal FOB orientation
6. Obtain required clinical images.

Figure 7:
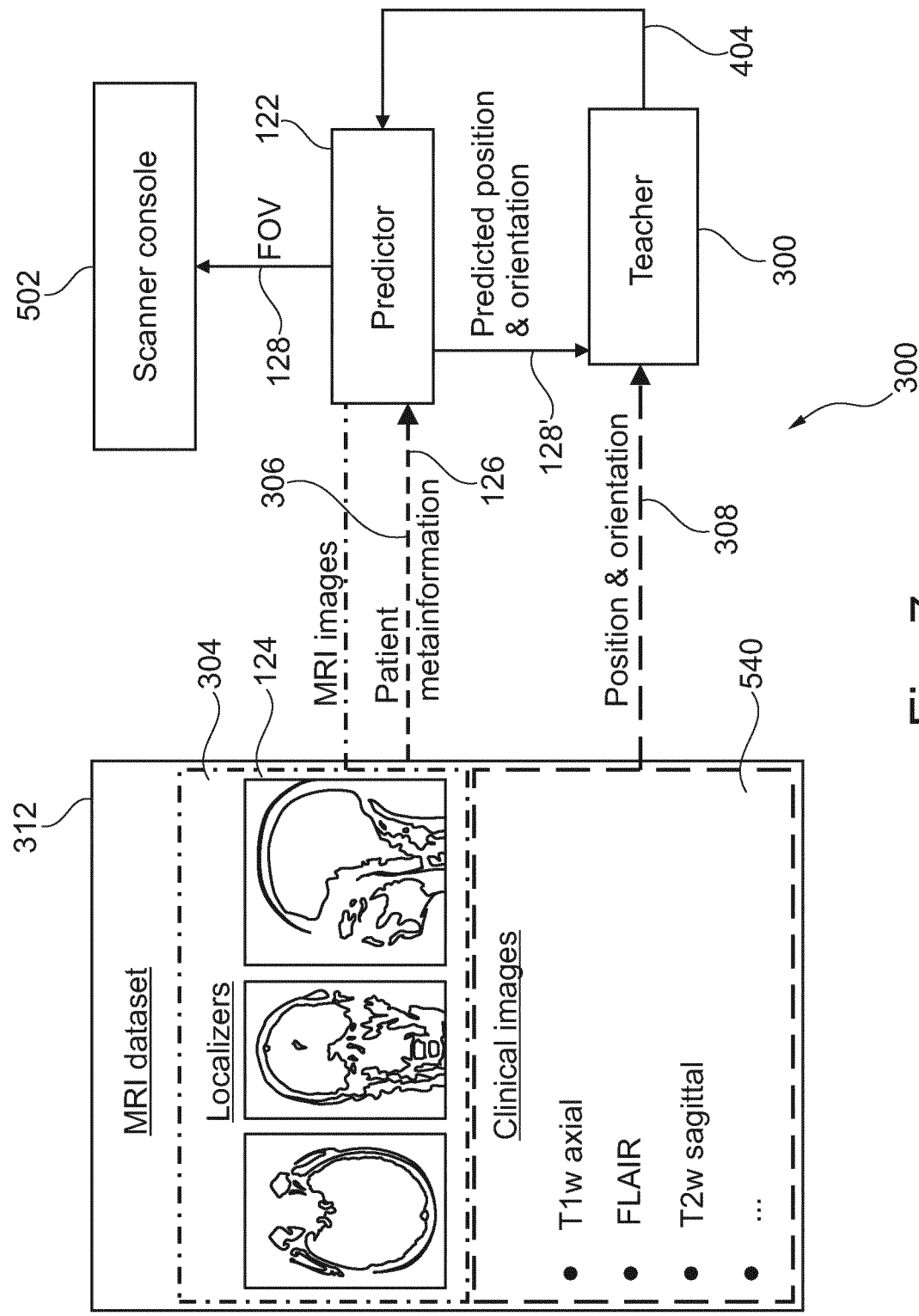
FIG. 7 illustrates a further example of a medical system.

FIG. 7 shows a functional view of a medical system 300. The medical system 300 may for example have access to a medical imaging database 312. This may contain historical magnetic resonance imaging data such as localizing magnetic resonance images which may be used as the one or more training magnetic resonance images 304. The medical imaging database 312 may also contain metadata descriptive of a subject which may be used as the training subject metadata 306. The one or more training magnetic resonance images 304 and the training subject metadata 306 may be input into the predictor algorithm 122. This may provide the predicted field of view alignment data 128' for the particular one or more training magnetic resonance images 304 and the training subject metadata 306. The predicted field of view alignment data 128' output by the predictor 122 may then be provided to the training algorithm 300. The medical imaging database 312 may also provide the field of view alignment data for the particular localizing images 304. This may be used as the training field of view alignment data 308. The training algorithm 300 may use the training field of view alignment data 308 and the predicted field of view alignment data 128' to then train 404 the predictor algorithm 122.

In other cases, the localizers may represent the one or more localizer magnetic resonance images 124 and the subject metadata 126. These may be input into the predictor algorithm 122 to generate the predicted field of view alignment data 128 which is then used to modify the pulse sequence commands and are used to control the magnetic resonance imaging system 502. For example, the scanner console or user interface 108 of the magnetic resonance imaging system 502 could display the predicted field of view alignment data 128 for approval by an operator.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 computer
104 processor
106 hardware interface
108 optional user interface
110 memory
120 machine executable instructions
122 predictor algorithm
124 one or more localizer magnetic resonance images
126 subject metadata
128 predicted field of view alignment data
128' predicted field of view alignment data
200 receive the one or more localizer magnetic resonance images and the subject metadata
202 receive the predicted field of view alignment data from the predictor algorithm in response to inputting the one or more localizer magnetic resonance images into the predictor algorithm and in response to inputting the subject metadata
300 training algorithm
302 training entry
304 one or more training magnetic resonance images
306 training subject metadata
308 training field of view alignment data
310 comparison
312 medical imaging database
400 receive the predicted field of view alignment data from the predictor algorithm in response to inputting the one or more training magnetic resonance images into the predictor algorithm and in response to inputting the training subject metadata
402 determine the comparison between the predicted field of view alignment data training field of view alignment data
404 train the predictor algorithm using the comparison between the predicted field of view alignment data and the training field of view alignment data
500 medical system
502 magnetic resonance imaging system
504 magnet
506 bore of magnet
508 imaging zone
509 region of interest
510 magnetic field gradient coils
512 magnetic field gradient coil power supply
514 radio-frequency coil
516 transceiver
518 subject
520 subject support
530 localizer pulse sequence commands
532 localizer magnetic resonance imaging data
534 clinical pulse sequence commands
536 modified pulse sequence commands
538 clinical magnetic resonance imaging data
540 clinical magnetic resonance image
600 acquire the localizer magnetic resonance imaging data by controlling the magnetic resonance imaging system with the localizer pulse sequence commands
602 reconstruct the one or more localizer magnetic resonance images from the localizer magnetic resonance imaging data
604 generate modified pulse sequence commands by modifying the clinical pulse sequence commands with the predicted field of view alignment data
606 acquire the clinical magnetic resonance imaging data by controlling the magnetic resonance imaging system with the modified pulse sequence commands

The invention claimed is:

1. A medical system comprising:
a memory configured to store machine executable instructions, predictor algorithm-configured to output predicted field of view alignment data for a magnetic resonance imaging system in response to inputting one or more localizer magnetic resonance images and subject metadata, wherein the predictor algorithm comprises a trainable machine learning algorithm, wherein the predictor algorithm is a convoluted neural network, and the memory further stores a training data, wherein the training data contains training entries, wherein each of the training entries comprises one or more training magnetic resonance images, training subject metadata, and training field of view alignment data; wherein the memory further comprises a training algorithm configured for training the predictor algorithm using a comparison between the predicted field of view alignment data and the training field of view alignment dat;
a processor configured to control the medical system, wherein execution of the machine executable instructions causes the processor to:
receive the predicted field of view alignment data from the predictor algorithm in response to inputting the one or more training magnetic resonance images into the predictor algorithm and in response to inputting the training subject metadata;
determine the comparison between the predicted field of view alignment data and the training field of view alignment data; and
train the predictor algorithm using the comparison between the predicted field of view alignment data and the training field of view alignment data;
receive the one or more localizer magnetic resonance images and the subject metadata; and
receive the predicted field of view alignment data from the predictor algorithm in response to inputting the one or more localizer magnetic resonance images into the predictor algorithm and in response to inputting the subject metadata.

2. The medical system of claim 1, wherein execution of the machine executable instructions further causes the processor to generate the training data by extracting the one or more training magnetic resonance images, the training subject metadata, and the training field of view alignment data from a medical image database.

3. The medical system of claim 1, wherein the medical system is any one of the following: a medical imaging workstation and a cloud based magnetic resonance imaging planning system.

4. The medical system of claim 1, wherein the medical system further comprises a magnetic resonance imaging system.

5. The medical system of claim 4, wherein the memory further comprises localizer pulse sequence commands configured to control the magnetic resonance imaging system to acquire localizer magnetic resonance imaging data, wherein execution of the machine executable instructions further causes the processor to:
acquire the localizer magnetic resonance imaging data by controlling the magnetic resonance imaging system with the localizer pulse sequence commands;
reconstruct the one or more localizer magnetic resonance images from the localizer magnetic resonance imaging data.

6. The medical system of claim 4, wherein the memory further comprises clinical pulse sequence commands configured for controlling the magnetic resonance imaging system to acquire clinical magnetic resonance imaging data, wherein execution of the machine executable instructions further causes the processor to:
generate modified pulse sequence commands by modifying the clinical pulse sequence commands with the predicted field of view alignment data; and
acquire the clinical magnetic resonance imaging data by controlling the magnetic resonance imaging system with the modified pulse sequence commands.

7. A computer program product comprising machine executable instructions stored on non-transitory computer readable memory for execution by a processor controlling a medical system, wherein the computer program product further comprises a predictor algorithm configured for outputting predicted field of view alignment data in response to inputting one or more localizer magnetic resonance images and subject metadata, wherein the predictor algorithm comprises a trainable machine learning algorithm, wherein the predictor algorithm comprises a trainable machine learning algorithm, wherein the predictor algorithm is a convoluted neural network, and the memory further stores a training data, wherein the 4rainingg data contains training entries, wherein each of the training entries comprises one or more training magnetic resonance images, training subject metadata, and training field of view alignment data; wherein the memory further comprises a training algorithm configured for training the predictor algorithm using a comparison between the predicted field of view alignment data and the training field of view alignment data, wherein execution of the machine executable instructions causes the processor to:
receive the predicted field of view alignment data from the predictor algorithm in response to inputting the one or more training magnetic resonance images into the predictor algorithm and in response to inputting the training subject metadata;
determine the comparison between the predicted field of view alignment data and the training field of view alignment data;
train the predictor algorithm using the comparison between the predicted field of view alignment data and the training field of view alignment data;
receive the one or more localizer magnetic resonance images and the subject metadata; and
receive the predicted field of view alignment data from the predictor algorithm in response to inputting the one or more localizer magnetic resonance images into the predictor algorithm and in response to inputting the subject metadata.

8. A method of operating a medical system, wherein the medical system comprises a memory storing a predictor algorithm, wherein the predictor algorithm is configured for outputting predicted field of view alignment data in response to inputting one or more localizer magnetic resonance images and subject metadata, wherein the predictor algorithm comprises a trainable machine learning algorithm, wherein the memory further stores training data, wherein the training data contains training entries, wherein each of the training entries comprises one or more training magnetic resonance images, training subject metadata, and training field of view alignment data; wherein the memory further comprises a training algorithm configured for training the predictor algorithm using a comparison between the predicted field of view alignment data and the training field of view alignment data, wherein the method comprises:
receiving the predicted field of view alignment data from the predictor algorithm in response to inputting the one or more training magnetic resonance images into the predictor algorithm and in response to inputting the training subject metadata;
determining the comparison between the predicted field of view alignment data and the training field of view alignment data; and
training the predictor algorithm with the training algorithm by inputting the comparison between the predicted field of view alignment data and the training field of view alignment data.

9. The method of claim 8, wherein the method further comprises generating the training data by extracting the one or more training magnetic resonance images, training subject metadata, and training field of view alignment data from a medical image database.

10. The method of claim 8, wherein the method comprises:
    receiving one or more localizer magnetic resonance images and subject metadata; and
    receiving the predicted field of view alignment data from the predictor algorithm in response to inputting the one or more localizer magnetic resonance images into the predictor algorithm and in response to inputting subject metadata.

11. The computer product of claim 7, wherein the memory further comprises:
    localizer pulse sequence commands configured to control the magnetic resonance imaging system to acquire localizer magnetic resonance imaging data, wherein execution of the machine executable instructions further causes the processor to:
        acquire the localizer magnetic resonance imaging data by controlling the magnetic resonance imaging system with the localizer pulse sequence commands; and
        reconstruct the one or more localizer magnetic resonance images from the localizer magnetic resonance imaging data.

12. The computer product of claim 7, wherein the memory further comprises: clinical pulse sequence commands configured for controlling the magnetic resonance imaging system to acquire clinical magnetic resonance imaging data, wherein execution of the machine executable instructions further causes the processor to:
    generate modified pulse sequence commands by modifying the clinical pulse sequence commands with the predicted field of view alignment data; and
    acquire the clinical magnetic resonance imaging data by controlling the magnetic resonance imaging system with the modified pulse sequence commands.

\* \* \* \* \*